United States Patent [19]

Folks et al.

[11] Patent Number: 4,752,565

[45] Date of Patent: Jun. 21, 1988

[54] CELL LINE PRODUCING AIDS VIRAL ANTIGENS WITHOUT PRODUCING INFECTIOUS VIRUS PARTICLES

[75] Inventors: Thomas M. Folks, Gaithersburg; Douglas M. Powell, Silver Spring; Malcolm A. Martin, Bethesda, all of Md.

[73] Assignee: The United States of America as represented by the Department of Health and Human Services, Washington, D.C.

[21] Appl. No.: 849,059

[22] Filed: Apr. 7, 1986

[51] Int. Cl.$^4$ .................. C12Q 1/70; C12N 15/00; C12N 7/04; C12N 5/00

[52] U.S. Cl. .................. 435/5; 435/172.1; 435/236; 435/237; 435/239; 435/810; 435/240.25; 436/808; 436/811; 436/813; 935/106; 935/110; 935/3; 530/808

[58] Field of Search .................. 435/172.1, 236, 237, 435/239, 240, 5, 810; 424/89; 436/501, 510, 536, 543, 808, 811, 813; 935/71

[56] References Cited

U.S. PATENT DOCUMENTS 4,520,113  5/1985  Gallo et al. .................. 436/531 X
4,659,599  3/1987  Gallo et al. .................. 435/240 X

OTHER PUBLICATIONS

Schüpback, J. et al., Science, 224:503–505 (1984).
Allan, J. S. et al., Science, 228:1091–1094 (1985).
Montagnier et al., Science 225:63–66 (1984).
Popovic et al., Science 224:497–500 (1984).
Chermann et al., Science 220:868–871 (1983).
Folks et al., Proc. Natl. Acad. Sci. USA 82:4539–4543 (1985).
Levy et al., Science 225:840–841 (1984).

*Primary Examiner*—Robert J. Warden
*Assistant Examiner*—Jack Spiegel
*Attorney, Agent, or Firm*—Holman & Stern

[57] ABSTRACT

Leu-3$^-$ cells surviving infection with the AIDS retrovirus can be induced with IUdR to express infectious virus. A cellular clone (8E5), isolated by limiting dilution of a mass culture of survivor cells, was found to contain a single, integrated, defective provirus that was consitutively expressed. Although IUdR treatment of 8E5 cells failed to induce infectious virus, cocultivation with Leu-3+ generated the characteristic syncytia associated with acute AIDS retrovirus infention. The single integrated copy of proviral DNA directs the synthesis of all major viral structural proteins except p64 and p34 as monitored by immunoblotting. Diagnostic reagents and kits in accordance with the present invention are also described.

6 Claims, 3 Drawing Sheets

FIG. 3A
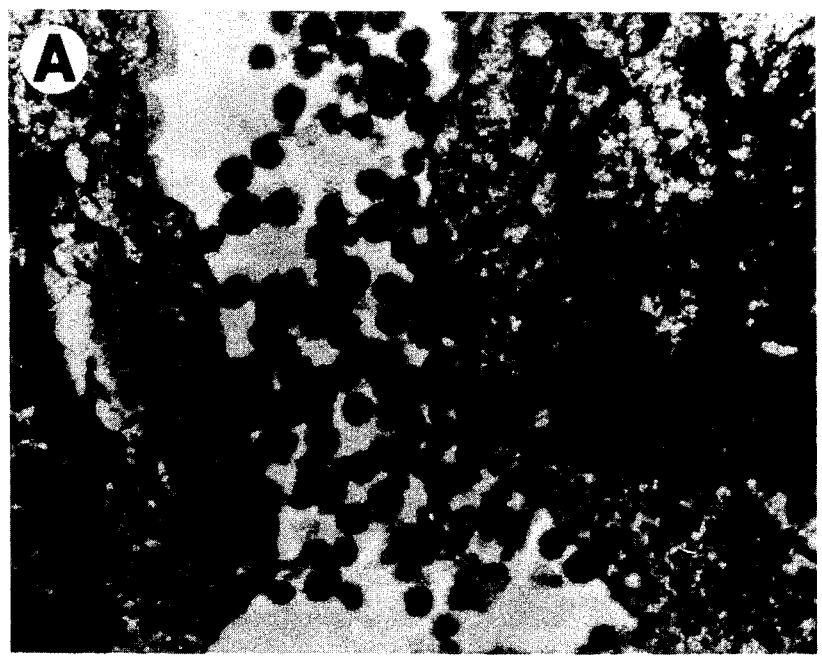
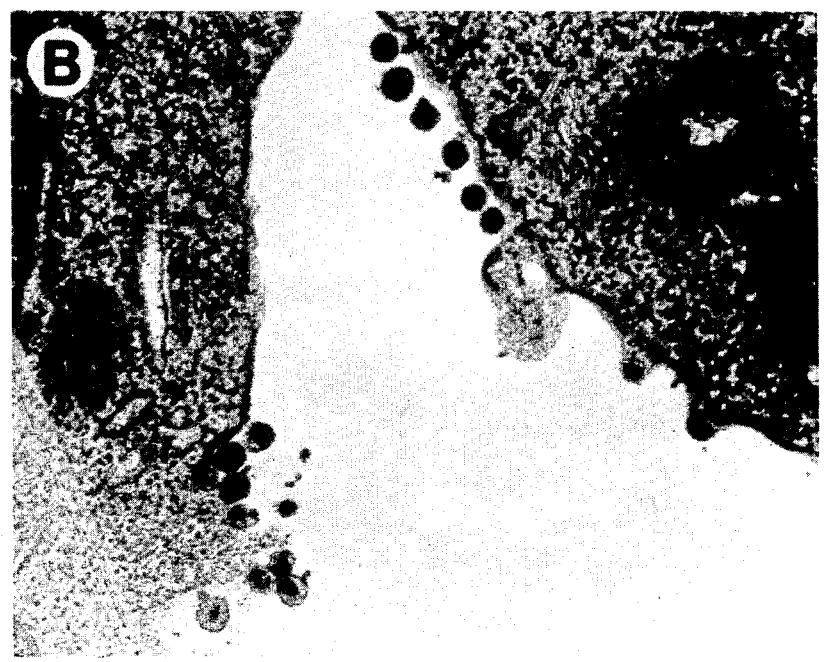
FIG. 3B

CELL LINE PRODUCING AIDS VIRAL ANTIGENS WITHOUT PRODUCING INFECTIOUS VIRUS PARTICLES

BACKGROUND OF THE INVENTION

1. Technical Field

The present invention is related to a virus which causes acquired immune deficiency syndrome (AIDS). More particularly, the present invention is related to obtaining a cell line capable of safely generating large quantities of the AIDS viral proteins without concomitant production of AIDS infectious viral particles.

2. State of the Art

AIDS is a fatal human disease that is most likely caused by a T lymphotropic human retrovirus (BarreSinoussi, et al., Science 220:868, 1983., Popovic et al., Science 224: 497, 1984; Levy, et al. Science 225: 840, 1984). It is believed that the virus is spread when body fluids, such as semen or blood from an infected individual, Holman & Stern, Chartered P49569 are passed to an uninfected person. Because a number of AIDS cases have been reported to result from the transfusion of contaminated blood, immunochemical testing of donor sera is being conducted to detect potential carriers. At present two types of screening tests are employed: enzyme-linked-immunoadsorbent (ELISA) assays and immunoblotting procedures. In both instances proteins isolated from purified virus particles or infected cell lysates are used as antigen to detect serum antibodies directed against the AIDS virus. The preparation of these viral antigens involves the handling of large volumes (about 50 liters/week) of infectious virus and tissue cultures. Presently, workers preparing these reagents cannot avoid continually being exposed to the infected materials and run the potential risk of contracting AIDS.

SUMMARY OF INVENTION

It is, therefore, an object of the present invention to provide a cell line capable of efficient production of AIDS viral antigens without concomitant production of infectious AIDS viral particles.

It is a further object of the present invention to provide a kit for the detection of AIDS-antibodies in a sample of the human body fluid or tissue, comprising containers containing AIDS viral antigen(s) produced by the cell line of the present invention and reagents or means for immunological determination of specific antigen-antibody reaction.

Other objects and advantages of the present invention will become apparent as the detailed description of the present invention proceeds.

BREIF DESCRIPTION OF DRAWINGS

These and other objects, features and many of the attendant advantages of the invention will be better understood upon a reading of the following detailed description when considered in connection with the accompanying drawings wherein:

FIG. 1 shows in situ hybridization of human T-lymphocyte lines synthesizing AIDS RV RNA. Photomicrographs of: 8E5 cells following (A) and prior (B) to treatment with IUdR; A3.01 cells 3 days post-infection (C) with the AIDS RV; uninfected A3.01 cells (D); IUdR inducible cells prior to (E) or following (F) incubation with IUdR. Magnifications are at ×400;

FIG. 2 shows the characteristics of AIDS RV DNA, RNA and proteins in 8E5 cells (A). 5.0 μg of 8E5 DNA was digested with EcoRI and analyzed by Southern blot hybridization using the pBenn6 probe. (B) Polyadenylated RNA was prepared from virus infected A3.01 (lane 1) or 8E5 (lane 2) cells and subjected to Northern analysis using a viral LTR probe. (C) Immunoblots of infected A3.01 (lane 1) or 8E5 (lane 2) cell lysates; numbers represent the molecular weights of the standard markers in terms of kilodaltons (kd) and the arrows indicate the position of the markers when subjected to electrophoresis under the conditions described; and FIG. 3 shows electron micrographs of AIDS RV particles synthesized from 8E5 (A) or virus infected A3.01 (B) cells. Magnifications are at ×50,000.

DETAILED DESCRIPTION OF INVENTION

Figure 1A:
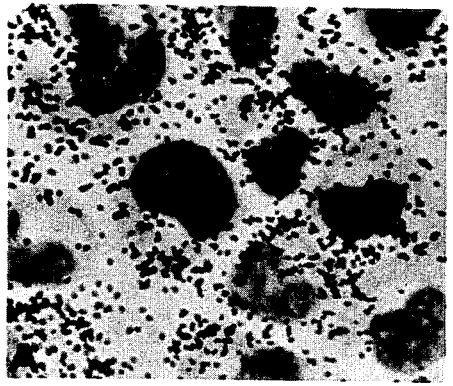

The above and other objects and advantages of the present invention are achieved by a unique human T lymphocyte line designated 8E5, having the characteristics of the deposit made at the American Type Culture Collection, Rockville, MD, under the accession number CRL8993. Upon issuance of a patent on the present invention, this deposit will continue to be viably maintained for 30 years and made available to the public without restriction, of course, consistent with the provisions of the law.

Although any methods and materials similar or equivalent to those described herein can be used in the practice or testing of the present invention, the preferred methods and materials are now described. All publications mentioned hereunder are incorporated herein by reference. Unless defined otherwise, all technical or scientific terms used herein have the same meaning as commonly understood by one of ordinary skill in the art to which this invention belongs.

A unique human retrovirus (RV) has been consistently isolated from patients with the acquired immunodeficiency syndrome (AIDS) and is believed to be the cause of AIDS. Infection of human T lymphocytes or T lymphocyte lines with the AIDS RV can result in a variety of outcomes ranging from rapid cell death to the integration of functionally inert proviral DNAs. A typical AIDS RV infection is characterized by the appearance of multinucleated cells, a burst of reverse transcriptase (RT) activity, and profound cellular degeneration that extends over a 5 to 20 day period. A recent report describes non-cytotoxic effects of the AIDS RV on human lymphocytes. In this report, phytohemagglutinin stimulated, interleukin-2 dependent cultures of helper-inducer human T cells exhibited the characteristic cytopathic effects of acute viral infection, but nonetheless, sufficient numbers of cells survived to continue to produce infectious virus during the four months they were maintained in culture (Hoxie et al. 1985, Science 229:1400).

Described herein is the discovery of Leu-3− non-virus producing cell, derived from a Leu-3+ T cell line, that survived infection with the AIDS RV which constitutively produces all of the major viral proteins except p64 and p34 but not infectious virus. This discovery is now presented in detail.

A cellular clone was isolated from a mass culture of survivor cells that contained a single copy of the AIDS RV provirus. The integrated proviral DNA was constitutively expressed but generated defective virus particles that failed to synthesize detectable reverse transcriptase. The methods and materials used in producing the cellular clone and in performing several tests and the like are described hereunder.

MATERIALS AND METHODS

Viral Infection, IUdR Induction, and Cell Cloning:

Beginning with a variant of the CEM T cell line (A3.01) which has been described by Folks et al., Proc. Natl. Acad. Sci. USA. 82:4539, 1985, approximately $2 \times 10^6$ A3.01 cells were infected with a $1 \times 10^{-3}$ dilution of an LAV strain of the AIDS RV stock in accordance with the procedure of Folks et al., supra. Following adsorption for 1 hour at 37° C., cells were washed and maintained ($1 \times 10^6$ cells/ml) in RPMI-1640 medium supplemented with 10% fetal calf serum. When the RT activity of the Leu-3− cultures which had survived infection became undetectable (7 to 10 days after the peak of RT), cells ($1 \times 10^6$/ml) were exposed to IUdR (100 µg/ml) for 24 h and then cocultivated with Leu-3+ A3.01 cells following standard technique well known in the art. The induction of virus was indicated by a second wave of RT activity in the cocultured cells; when RT was no longer detectable, the survivor cells were subjected to a second cycle of IUdR induction/cocultivation. The RT negative, Leu-3− cells surviving these treatments were cloned by the standard limiting dilution technique in 96 well microtiter plates. One hundred eleven single cell clones were obtained, pooled into groups of 10, expanded to a total of $1 \times 10^6$ cells, exposed to IUdR for 24 h, cocultivated with Leu-3+ A3.01 cells, and examined daily for expression of the AIDS RV by monitoring syncytia formation. A single clone (8E5) was thus obtained.

Nucleic Acid Hybridization: DNA and RNA were prepared from AIDS RV infected cells or 8E5 cells and analyzed for the presence of virus-related sequences by Southern or Northern blot hybridization utilizing cloned LTR (long terminal repeat) or representative gag-pol-env probes as described by Folks et al., 1985, Proc. Natl. Acad. Sci. USA 82:4539; Rabson et al., 1985, Science 229:1388; Benn et al., 1985, Science 230:949. For in situ hybridization, cultured cells were sedimented onto polylysine coated glass slides, fixed in periodate-lysine-paraformaldehyde-glutaraldehyde (PLPG) and pretreated with HCl and proteinase K to allow the labeled probe to enter the cells as described by Gendelman et al., 1983, J. Immun. Meth. 65:137; Gendelman et al., Proc. Natl. Acad. Sci. USA 82:7086. Cells were prehybridized in 10 mM Tris pH 7.4, 2X standard saline citrate (SSC) (1X SSC is 0.15M NaCl, 0.015M sodium citrate, pH 7.4), 50% formamide, 1 ×Denhardt's solution (0.02% polyvinylpyrrolidone, 0.02% Ficoll, 0.02% bovine serum albumin) and 200 µg/ml yeast tRNA at 45° C. for 2 h and hybridized in this solution containing, 10% dextran sulfate, 5µM dithiothrietol and $10^6$ counts/min of $^{35}$S-labeled AIDS RV RNA in 10 µL reaction mixtures. Subgenomic viral DNA fragments present in pB1 (Benn et al, supra), pBenn6 (Folks et al., supra), pB11 (Benn et al, supra), and a recombinant plasmid (pRG-B), which contains a 1.35 kb HindIII fragment mapping between 8.25 and 9.6 kb on the proviral DNA, were subcloned into SP6/T7 vectors (Promega Biotec, Madison, WI) and the pooled DNAs transcribed using ±S-UTP (Amersham Corp., Arlington Hgts., IL). The labeled RNAs were incubated with 40 µM $NaHCO_3$ -60 µM $Na_2 CO_3$, pH 10.2 prior to hybridization to facilitate their entry into cells.

In situ hybridization was performed at 45° C. for 8 h. The samples were then washed in: 2×SSC at 22° C. for 10 min ×2 changes; 2×SSC, 0.1% Triton ×100 at 60° C. for 30 min; 2×SSC with RNase A (40 µg/ml) and RNase $T_l$(10 U/ml) at 37° C. for 30 min; and 2×SSC at 60° C. for 10 min. All solutions excluding those with RNase contained 5 µM DTT and 1 µM EDTA. Autoradiography was performed for 1-2 days following standard procedures well known in the art.

To control the specificity of in situ hybridization, probes synthesized in the sense orientation (same polarity as viral mRNA) were incubated with duplicate cell preparations; in addition, uninfected cells were hybridized with antisense probes (such as complementary to viral mRNA). Infected cell preparations were also treated with RNase prior to addition of the probe.

Immunoblotting: Total cell lysates prepared from AIDS RV infected A3.01 or 8E5 ($1 \times 10^8$) cells were boiled in 2% SDS and 2-mercaptoethanol and electrophoresed through 3-27% gradient polyacrylamide gels at about 100 volts for about 18 hrs. (Integration Separation Sciences) by the method of Laemmli, 1970 Nature 227:680 and transferred to nitrocellulose membranes (Towbin et al., 1979, Proc. Natl. Acad. Sci. USA 76:4350). The filters were then treated with 5% nonfat dry milk in 10 µM NaCl (TN) for 30 min and further rinsed in TN buffer containing 0.3% Tween-20, 0.5% NP40 (TN-TN) and 1% BSA. Pooled AIDS patients sera (1:1000), diluted in TN-TN containing 3% BSA, were incubated with the nitro-cellulose filters overnight at room temperature. The membranes were then washed 3×in TN-TN buffer, incubated for 2 h with $^{125}$-protein A (200,000 dpm/ml), washed, air dried, and exposed to x-ray film in accordance with techniques well known in the art.

Electronmicroscopy: A3.01 cells infected with the AIDS retrovirus, or 8E5 cells, were centrifuged at 650×g in standard Beem capsules. The pellets were then gently washed in serum-free RPMI 1640 medium and fixed in situ for 1-2 h in 2.5% gluteraldehyde in the presence of 0.1M sodium cacodylate buffer, pH 7.2. Following three 5 min washes in 0.1 M sodium cacodylate buffer containing 4% sucrose, the pellets were treated with 1% osmium tetroxide for 1-2 h. They were then washed three times in 0.1M sodium cacodylate buffer and dehydrated in 30 to 100% ethanol, followed by a final dehydration using propylene oxide. The samples were then embedded in epon-Araldite LX-112 (Ladd Research Industries, Burlington, VT) and thin sections were prepared. After sequential staining with lead acetate and uranyl acetate, the preparations were examined in a JEOL 100B electronmicroscope at 80 KV.

By the methods described herein, a single clone (8E5) was isolated that produced syncytia with cocultured Leu-3+ A3.01 cells following exposure to IUdR. When 8E5 cells were expanded and characterized in greater detail, an unanticipated result was obtained. Despite repeated treatments with IUdR, no RT activity could be detected in the cocultures of 8E5 and the Leu-3+ A3.01 cells that were maintained for more than 30 days. This was surprising in view of the readily demonstable syncytia that appeared 24 h following IUdR treatment of the 8E5 cells.

Figure 1B:
Figure 1C:
Figure 1D:
Figure 1E:
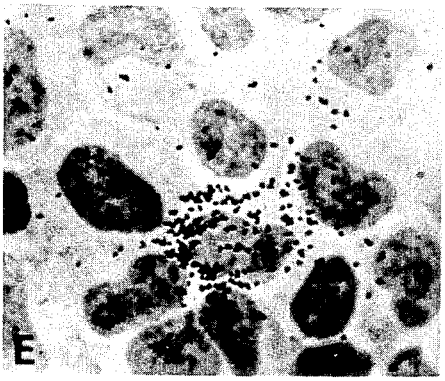
Figure 1F:
Figure 2A:
Figure 2B:
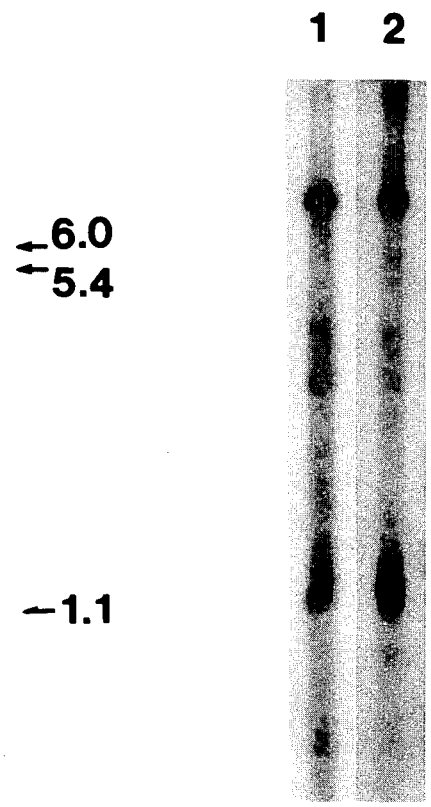

Detection of viral RNA, DNA, and protein in 8E5 cells. Since it was unclear which, if any, AIDS RV gene products were being expressed in induced 8E5 cells, in situ hybridization was employed to monitor the IUdR effect. As shown in FIG. 1A, virtually all of the IUdR treated 8E5 cells synthesized viral RNA. Of interest was the fact that 8E5 cells, growing in the absence of IUdR, also expressed high levels of AIDS RV RNA (FIG. 1B). The in situ hybridization results shown in FIG. 1 also indicated that cloned 8E5 cells contained comparable amounts of viral mRNA as that present in a cell infected with virus (FIG. 1C). To more fully evaluate the RNA present in the 8E5 clone, polyadenylated RNA was isolated and examined by Northern blot hybridization using an LTR probe as mentioned herein supra. FIG. 2B shows that similar to A3.01 cells which actively produce virus, uninduced 8E5 cells also contain substantial amounts of 9.1 (genomic/gag-pol), 5.0, 4.3 (env), and 1.8–2.0 kb viral RNAs. Although this Northern analysis suggested that the expression of the 5.5 kb species of viral RNA might be reduced in 8E5 cells, S1 nuclease protection experiments (data not shown) indicated that RNAs processed at the putative splice acceptor for 5.5 kb viral RNA were readily identified.

The number and state of proviral DNA copies in 8E5 cells was analyzed by Southern blot hybridization of $EcoR_I$ digested cellular DNA. Since the parental LAV provirus contains two internal $EcoR_I$ restriction sites defining a 1.1 kb viral DNA segment, the presence of only three reactive cleavage products (FIG. 2A) is consistent with the clonality of the 8E5 line and the existence of a single integrated copy of viral DNA.

Figure 2C:
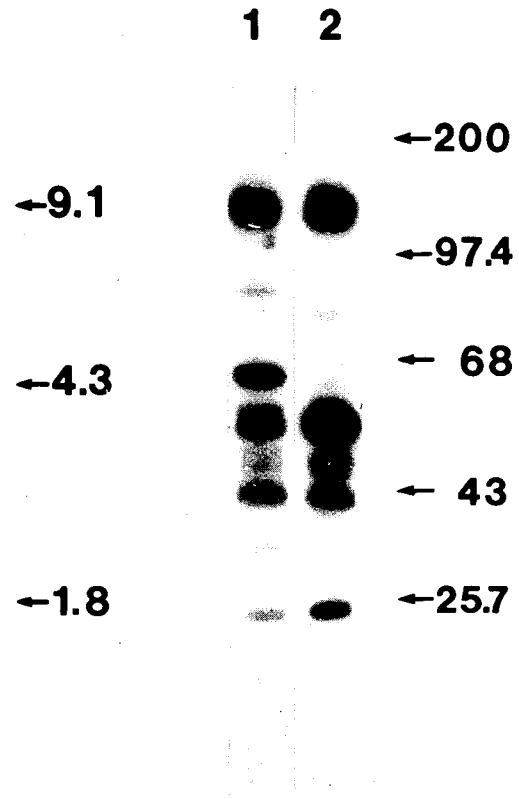

These results clearly indicate that the one copy of the LAV provirus in 8E5 cells is constitutively expressed as viral RNA but provides no explanation for the absence of RT activity subsequent to IUdR treatment. As a first step toward identifying this abnormality, the viral proteins present in 8E5 cells were analyzed by immunoblotting using pooled AIDS sera. A side-by-side comparison with the immunoreactive polypeptides present in virus-producing A3.01 cells (FIG. 2C) evidences the presence of major viral encoded glycoprotein gp120, and polypeptides p55, p41, and p25 (as well as others not shown) and the absence of the prominent 64 kd and fainter 34 kd (kilodalton) viral polypeptides in 8E5 cells. It is noted that other proteins having molecular weights of 160K, 90K, 46K, 43K and 17K are also produced. A similar immunoblot was obtained when a lysate, prepared from 8E5 cells treated with IUdR, was examined (data not shown).

When 8E5 cells were examined electronmicroscopically, innumerable retrovirus-like structures were visualized budding from their surface (FIG. 3). These particles are readily distinguished from infectious virions produced in A3.01 cells because they lacked the condensed rod-shaped nucleoid characteristic of the AIDS RV.

The tissue culture medium from untreated or IUdR treated 8E5 cells was also examined for the presence of infectious virus particles. Supernatants, concentrated from $1 \times 10^8$ 8E5 cells, were incubated with $2 \times 10^6$ Leu-3+ A3.01 cells as described by Folks et al, supra, in an attempt to amplify any released viral particles. In repeated experiments, the synthesis of infectious progeny virions, as monitored by RT assays, was invariably negative. Nonetheless, A3.01 cells, exposed to concentrated 8E5 tissue culture supernatants, did exhibit minimal syncytia formation. However, the development of syncytia could not be demonstrated following the serial (and blind) passage of the 8E5 supernatant through A3.01 cells.

In situ hybridization of IUdR inducible cells. Since the characterization of the cloned 8E5 survivor cell indicated the presence of a single copy of proviral DNA that directed the synthesis of defective virus particles, an effort was made to determine how and when this cell arose. Accordingly, in situ hybridization was used to evaluate the IUdR inducible cells which survived the initial infection with LAV. As shown in FIG. 1E, cells constitutively expressing AIDS RV mRNA could be identified in the mass culture of IUdR inducible cells. These cells existed at a frequency of $\geq 1/1000$ at least two IUdR/cocultivation cycles prior to the isolation of the 8E5 clone. In the presence of IUdR, the level of viral RNA synthesis in the survivor cells did not appreciably change (FIG. 1F).

Folks et al., 1986 (Science 231:600–602) reported that IUdR treatment of virus-free, Leu-3− lymphocytes surviving infection with the AIDS RV induced infectious virus as monitored by RT assays. The IUdR induced progeny virions as described by Folks et al., 1986, supra (incorporated herein by reference) were indistinguishable from their LAV parent in terms of tropism for Leu-3+ lymphocytes, the cytopathic effect that occurred during their replication in human T cells, and in their kinetics of infection. Although, prior to analysis, one would generally expect to have cloned in the 8E5 cell an IUdR inducible survivor cell that contained a "wild-type" provirus, it was indeed surprising when the analysis revealed that 8E5 cells in fact harbored a defective copy of the AIDS viral DNA.

It should also be noted that the presence of the AIDS RV proviral DNA and the synthesis of all major viral proteins except p64 and p34 have no effect on cell viability. Thus, if a viral encoded protein, rather than the complex process of virus replication, is responsible for viral CPE and cell death, such a protein is, of course, not synthesized in 8E5 cells and the characterization of such a protein would offer an important clue as to the factor responsible for the deadly infectivity of the AIDS virus.

Some examples of the useful applications of the present invention are now described.

1. 8E5 cells are maintained in RPMI-1640 plus 10% fetal calf serum at approximately $1-5 \times 10^6$ cells/ml. Both supernatants and whole cells are used for extraction/purification of viral particles/protein for biochemical analysis such as protein sequencing. This is accomplished by large scale purification (greater than 10 liter of culture material).

2. Supernatant material containing 8E5 virus particles is harvested and purified for use in ELISA and immunoblotting kits for antibody detection (blood screening).

3. Cellular material from 8E5 cells is harvested and used as viral antigen for detection of antibodies in immunoblotting kits (blood screening).

4. 8E5 cells are harvested and used as viral antigen source for antibody detection in immunofluorescent diagnostic kits or in flow cytometric analytical assays.

5. Monoclonal antibodies are made against 8E5 viral antigens which react against HTLV-III/LAV antigens. 8E5 viral antigens are inoculated into mice or rats and lymphoid cells from these animals are fused with tumor cells to form stable monoclonal antibody producing hybridomas following standard techniques.

6. 8E5 proviral DNA is isolated and molecularly cloned for use in transforming lymphoid and non-lymphoid cells of different mammalian species for the constitutive production of viral proteins.

7. Purified 8E5 cells or particles are used for inoculation of non-human primates, other animals, and humans, for vaccine development.

8. 8E5 cells are used for target cells in cell mediated and complement mediated cytotoxicity assay systems.

9. 8E5 particles are used to biologically modify HLA matched target cells for use in cell mediated cytotoxicity assays.

10. 8E5 cells are used as a safe standard of cloned HTLV-III/LAV antigen source for nucleic acid in situ hybridization and immuno-fluorescent antibody assays.

It is understood that the examples and embodiments described herein are for illustrative purposes only and that various modifications or changes in light thereof will be suggested to persons skilled in the art and are to be included within the spirit and purview of this application and the scope of the appended claims.

We claim:

1. A cell line capable of producing AIDS viral materials without producing infectious viral particles, and having the characteristics of ATCC CRL 8993.

2. A non-infectious AIDS virus obtained from the cell line of claim 1.

3. The non-infectious AIDS virus of claim 2, comprising the following antigenic virus proteins having molecular weight in kilodaltons of, 120, 90, 55, 46, 43, 41, 24, 17 and lacking viral proteins of 64 and 34 kilodalton as determined by immuno-blot analysis in 3%-27% polyacrylamide gel electrophoresis in the presence of mercaptoethanol.

4. The AIDS virus of claim 2 having specific binding affinity for AIDS virus antibodies.

5. A composition of matter, comprising an antigenic amount of the non-infectious AIDS virus of claim 2.

6. A kit for detecting the presence of AIDS related material comprising containers containing the cell line of claim 1 or products obtained from cell line.

* * * * *